United States Patent [19]

Wu

[11] Patent Number: 5,172,830
[45] Date of Patent: Dec. 22, 1992

[54] COTTONBUD DISPENSER

[76] Inventor: Ching-Kao Wu, Room 2, 11th Fl., No. 85, Shoei-Yuan Road, Taipei, Taiwan

[21] Appl. No.: 746,370

[22] Filed: Aug. 16, 1991

[51] Int. Cl.⁵ ............................................. B65G 59/00
[52] U.S. Cl. .................................. 221/131; 221/250; 221/276; 221/287
[58] Field of Search ............... 221/268, 270, 276, 124, 221/131, 287, 247, 250

[56]  References Cited
U.S. PATENT DOCUMENTS

| | | | |
|---|---|---|---|
| 1,624,883 | 4/1927 | Allen | 221/131 |
| 1,677,938 | 7/1928 | Van Sickle | 221/276 |
| 2,211,349 | 8/1940 | Nye | 221/250 |
| 3,242,930 | 3/1966 | Wilner | 221/276 |
| 3,351,233 | 11/1967 | Chanoch et al. | 221/276 |

FOREIGN PATENT DOCUMENTS 478699  11/1969  Switzerland .................. 221/276

Primary Examiner—H. Grant Skaggs
Attorney, Agent, or Firm—Bacon & Thomas

[57]  ABSTRACT

A cottonbud dispenser consisting of a base, a plurality of long coiled springs, pushing blocks to push said springs, a position block, a fixing plate, a stop plate and a transparent case body storing cottonbuds, any of said pushing blocks below the base being possible to be pushed to eject a cottonbud in one of the rooms in the base to extend out of said room so as to be picked up by fingers and also possible to be pushed back to its original position by the compressed long spring after said pushing block is released.

5 Claims, 6 Drawing Sheets

COTTONBUD DISPENSER

BACKGROUND OF THE INVENTION

A conventional cottonbud or swab case as shown in FIG. 2 generally has a cylindrical container 10 closed with a lid 11, which may often be taken off with excessive force by a user so as to force some of the cottonbuds stored therein to drop out of the container 10. In addition, extra cottonbuds may carelessly and easily be pulled out together with the one chosen to be picked up, and worse, the cotton balls at both ends of the sticks may be contaminated when being picked up. Due to the spreading-out of the upper ends of the cottonbuds, as shown in FIG. 1, the cottonbuds need to be pushed to stand upright before the lid 11 may be placed on the container 10, which makes the cottonbud case quite inconvenient to handle when the lid 11 is taken off to pick up a cottonbud.

SUMMARY OF THE INVENTION

In view of the disadvantages of a conventional cottonbud case, the present cottonbud dispenser has been devised to have the following advantages:

1. Cottonbuds are stored lengthwise in a case body and can be pushed out one by one by a pushing block manually pulled so as to be picked up by fingers without touching cotton balls at both ends of a stick.

2. A case body stored with cottonbuds can be easily replaced by a new case body fully stored with cottonbuds if all of the cottonbuds in the old one are used up.

3. Cottonbuds stored in the case body can be taken out one by one without the inconvenience of having them drop out of the case body.

DETAILED DESCRIPTION OF THE INVENTION

Figure 1:
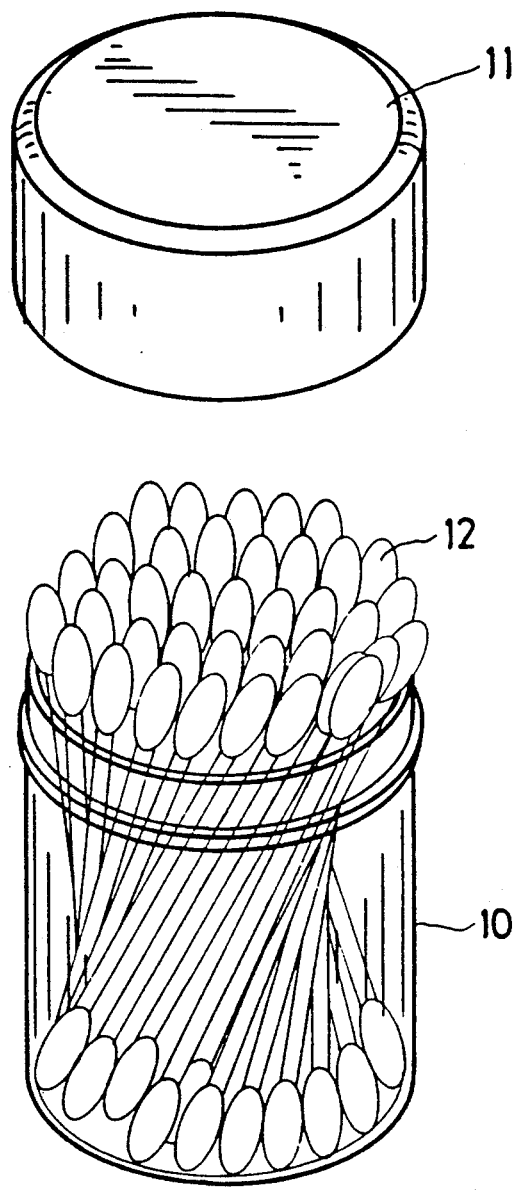
FIG. 1 is a perspective view of a conventional cottonbud case with cottonbuds stored therein.
Figure 2:
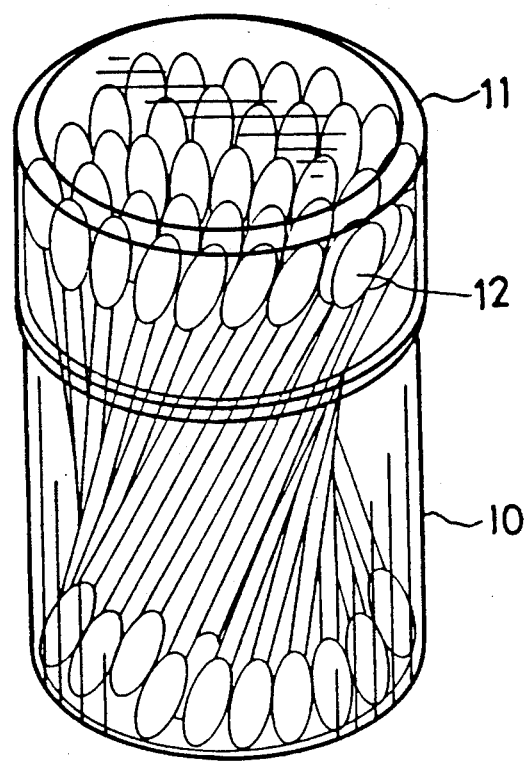
FIG. 2 is a perspective view of a conventional cottonbud case.
Figure 3:
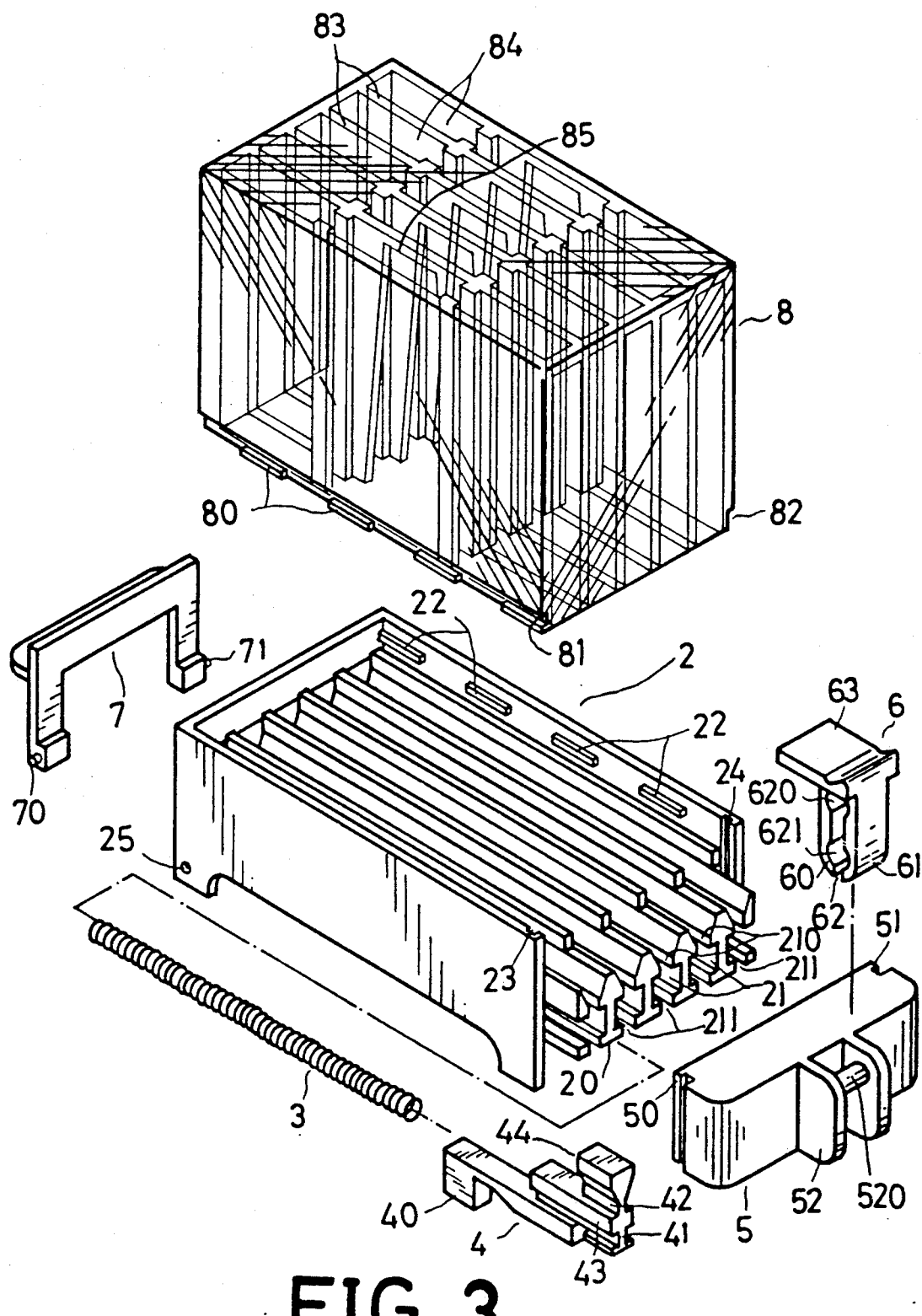
FIG. 3 is an exploded perspective view of a cottonbud dispenser of the present invention.

A cottonbud dispenser in accordance with the present invention, as shown in FIG. 3, comprises a rectangular base 2, a plurality of long coiled springs 3, the same number of pushing blocks as the springs 3, a position block 5, a reverse L-shaped fixing plate 6, a reverse U-shaped stop plate 7 and a case body 8 as the main components.

The rectangular base 2 has its interior divided with a plurality of lengthwise separating boards 20 equally spaced apart to form a plurality of rooms 21, each of which has a lengthwise opening 210, 211 respectively at the upper and the lower portion. The base 2 also has a row of several short ridges 22 spaced apart on both lengthwise upper inner walls, vertical grooves 23, 24 respectively in both right ends of the lengthwise inner walls, a fitting hole 25, 26 (fitting hole 26 is not shown in the drawings) in both right ends of the lengthwise sides, the same number of exits 27 as the rooms 21 in the left side communicating with the rooms 21.

The same number of long coiled springs 3 and of pushing blocks 4 as the rooms 21 are respectively placed in each room 21 in series so that said blocks 4 can manually push said springs 3.

The pushing blocks 4 are provided with a pulling grip 40 extending down at the left side, two I-shaped guide rails 41, 42 at the right upper section sandwiching a blocker 43, and a pushing piece 44 on the rail 42.

The position block 5 is to be combined with the base 2, having two vertical ridges 50, 51 respectively on both sides of the left vertical wall to fit in the vertical guide grooves 23, 24 of the base 2, a rod supporter 52 and a rod 520 held between two parallel walls of the rod supporter 52.

The reverse L-shaped fixing plate 6 is to be sustained on the rod 520 in the supporter 52, having two downward spaced-apart pinch arms 60, 61 forming an opening 62 and two circular holes 620, 621 in line and a flat square block 63 extending leftward at the top.

The reverse U-shaped stop plate 7 is to be combined with the base 2 at its left side to normally stop the exits 27 in the left side of the base 2, having two projections 70, 71 respectively at the lower ends of the two vertical portions to fit in fitting holes 25, 26 in the base 2 to make said stop plate 7 turn down with the projections 70, 71 as pivots.

The rectangular case body 8 is made of transparent material to be positioned on the base 2, having four side walls and a top wall but no bottom wall, several spaced-apart ridges 80 in line on both bottom edges of the lengthwise sides to form two guide grooves 81, 82, a plurality of same-sized separating boards 83 equally spaced apart in the interior, two neighboring boards 83 forming a room 84 for storing cottonbuds horizontally and lengthwise. Each separating board 83 has a large opening in the middle portion facing to the bottom. The number of the rooms 84 is the same as that of the rooms 21 in the base 2. To load cottonbuds in the case body 8, said case body 8 is to be held upside down, and cottonbuds are to be put in each room 84 through the bottom. When the case body has been loaded fully with cottonbuds, then said case body can be assembled with the base 2 also held upside down on the case body 8, which is to be pulled from the right to the left making the ridges 80 to fit in the spaces among the ridges 22 so as to make the case body 8 sit on the base 2 and each room 84 lengthwise communicate with each room 21 in the base so that the lowest cottonbud in each room 84 can go down in the corresponding room 21 in the base 2.

Figure 4:
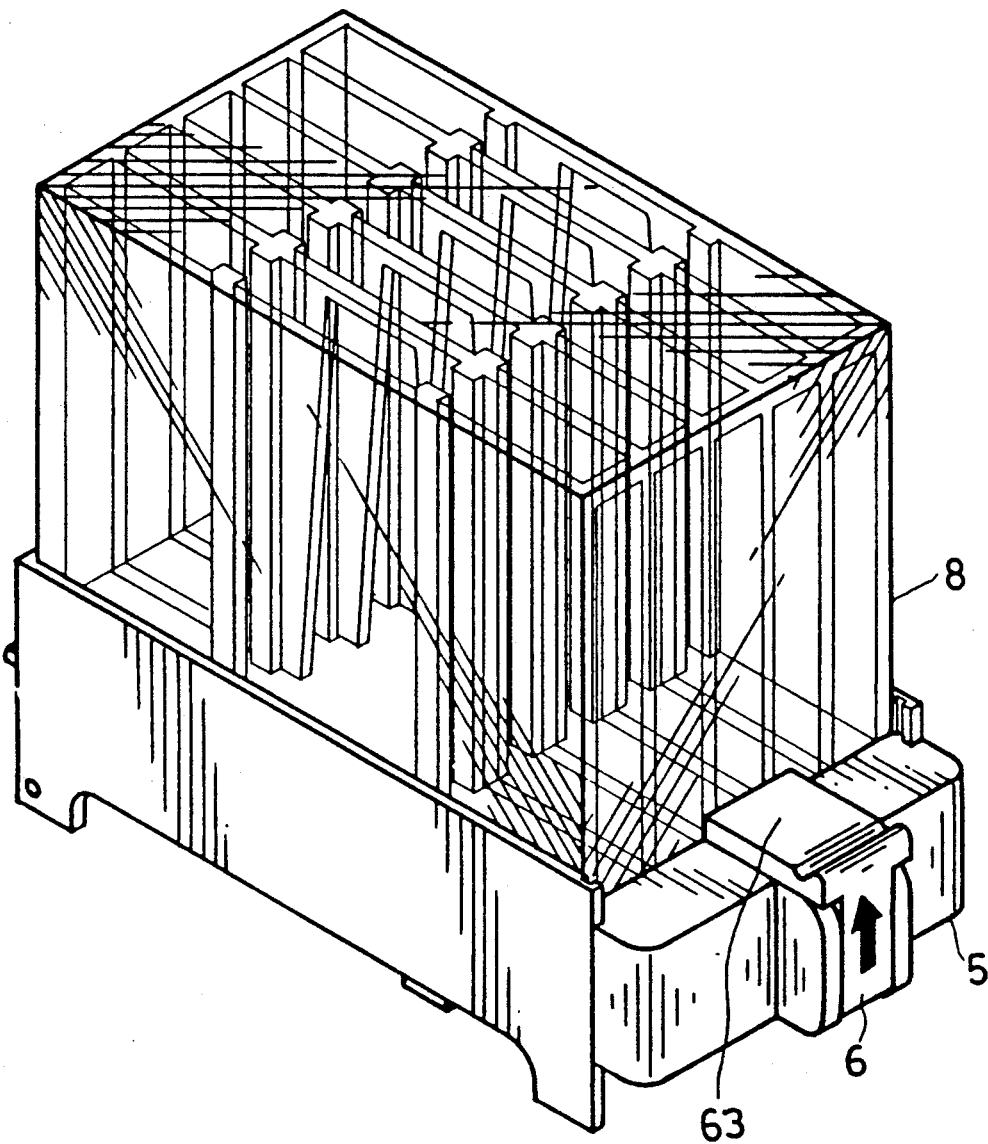
FIG. 4 is a perspective view of a cottonbud dispenser of the present invention.
Figure 5:
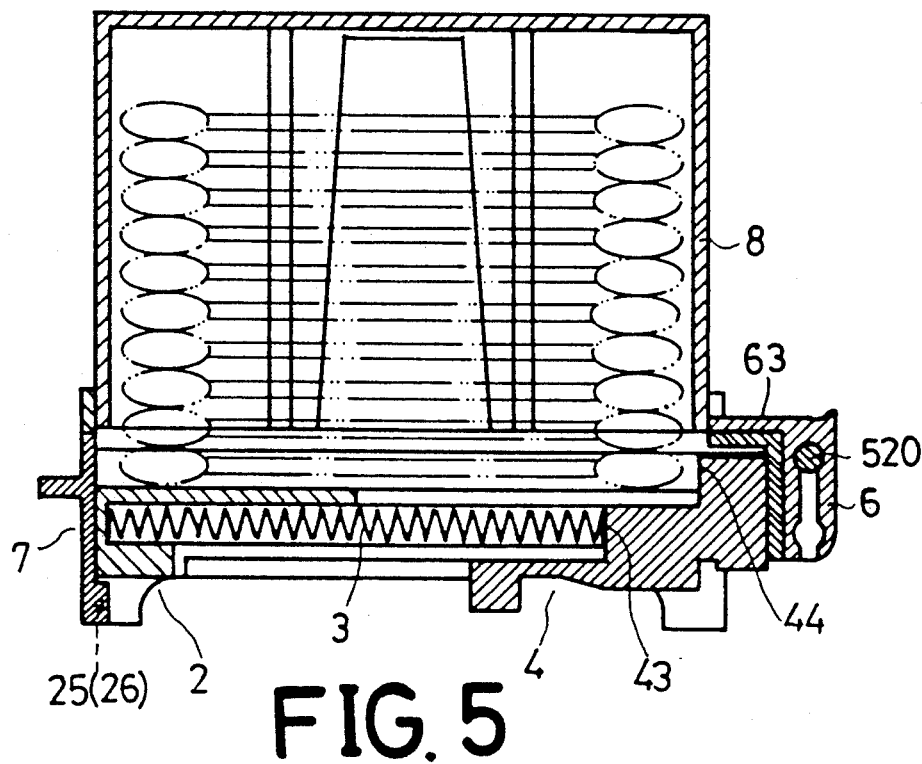
FIG. 5 is a cross-sectional view of a cottonbud dispenser of the present invention.

In assembling this cottonbud dispenser, at first, the springs 3 and the pushing blocks 4 are to be placed in series in the rooms 21 in the base 2, with one end of each spring 3 resting on the left end of the blocker 43 of each pushing block 4. At the same time, the pulling grip 40 extends downward out of each room 21, the guide rails 41, 42 respectively fit and can move in the lengthwise openings 210, 211, and the pushing piece 44 extends in the opening 210. Next, the position block 5 is to be combined with the base 2, by fitting both ridges 50, 51 in the guide grooves 23, 24. Then the case body 8 stored with cottonbuds is to be assembled with the base 2, by holding said case body 8 upside down and the base 2 also upside down and pushing said case body 8 from the right to the left under the base 2, with the ridges 80 fitting in the spaces among the ridges 22. Then they are to be turned upside down again after assembled together. Next, the reverse L-shaped fixing plate 6 is to be combined with the position block 5, by pushing down said plate 6 and placing the circular hole 620 fitting with the rod 52 as shown in FIGS. 4 and 5. Thus, the flat block 63 of the reverse L-shaped fixing plate 6 can keep the case body 8 in place, preventing the case body 8 from moving off the base 2. Lastly, the reverse U-shaped stop plate 7 is to be combined with the base 2, with the projections 70, 71 fitting in the holes 25, 26 and making the stop plate 6 to stand close beside the left side of the base 2 so as to keep the cottonbuds in the case body from moving out of the exits 27.

Figure 6:
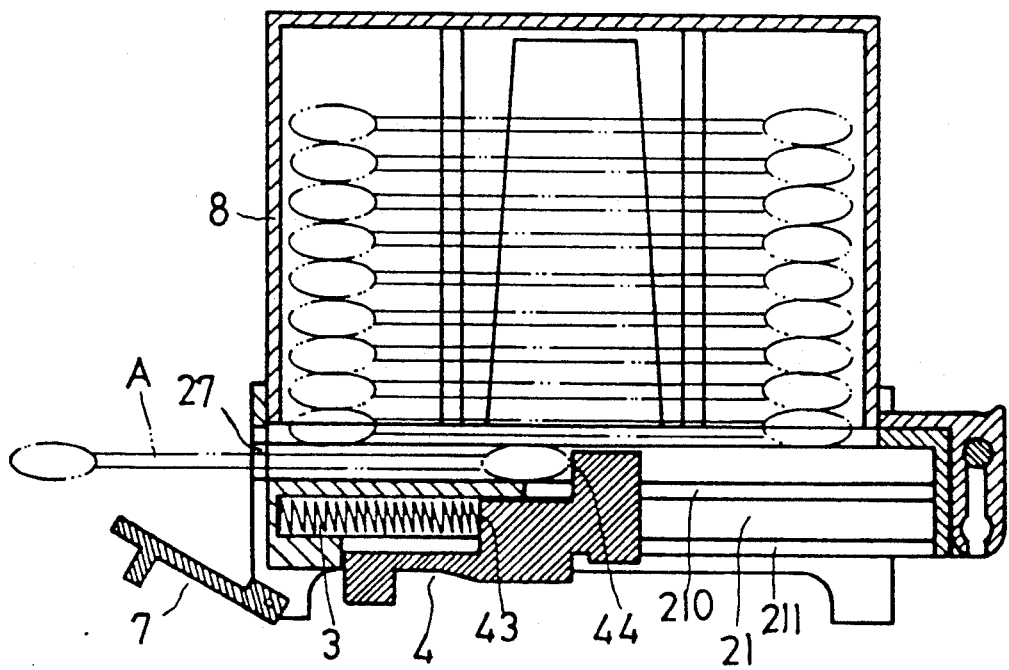
FIG. 6 is a cross-sectional view of a cottonbud dispenser with a cottonbud dealt out in the present invention.

In order to take out a cottonbud from the cottonbud dispenser, any of the pushing blocks 4 below the base 2 as shown in FIG. 6 can be pushed with a finger to the left, and the pushing piece 44 will push a cottonbud A to the left out of one of the rooms 21 to be picked by fingers. And simultaneously, the blocker 43 will force and compress one of the springs 3, and the reverse U-shaped stop plate 7 will be pushed open by the cottonbud A. After the cottonbud has been taken out of the base 2, the pushing block 4 can elastically be pushed back to its original position by the compressed spring 3 elastically lengthening as shown in FIG. 5, and becomes ready for next manipulation, after the lowest cottonbud in the room 84 has dropped down in the room 21 where the cottonbud had just been taken out from.

Figure 7:
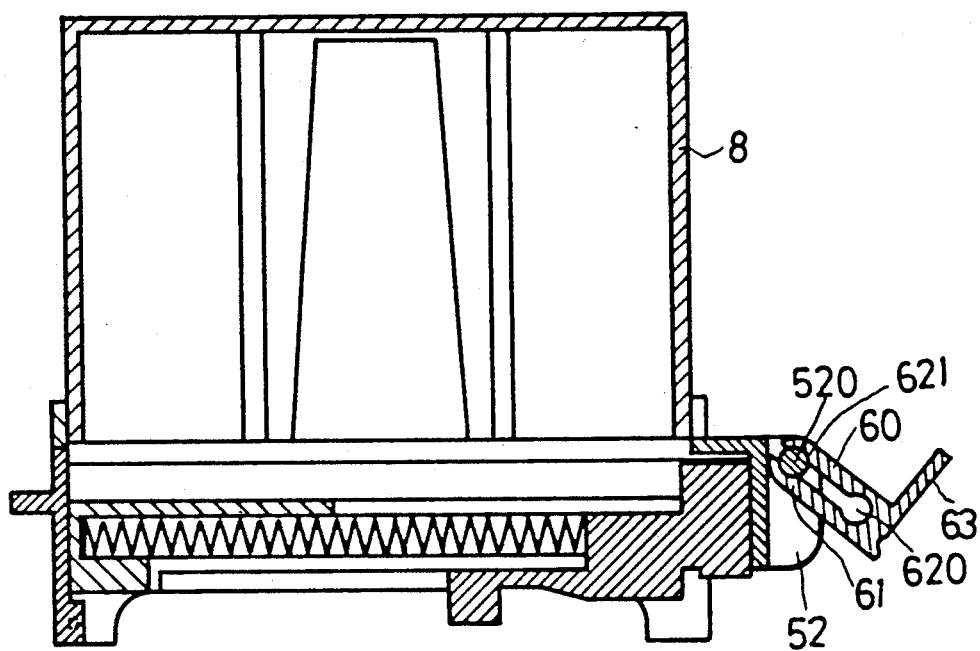
FIG. 7 is a perspective view of the case body prepared to be taken off the base with the fixing plate pulled down in the present invention.

When all of the cottonbuds A stored in the case body 8 have been taken out, the reverse L-shaped fixing plate 6 is to be pulled up as shown in FIG. 7, placing the lower circular hole 621 to fit with the rod 520, and then said plate 6 is to be pulled down to the right with the rod 520 as a pivot. Now the flat plate 63 can no longer keep the case body 8 in its position, which can be taken off the base 2, by pulling the case body 8 horizontally from the left to the right. Then a new case body 8 loaded with cottonbuds can be assembled with the base 2 in place of the old one, in the way mentioned above.

What is claimed is:

1. A cottonbud dispenser comprising:
a) a base having rooms separated by vertical separating boards, wherein each of said rooms is provided with an opening in the upper and the lower portion of said rooms, and wherein said base has two or more vertical walls, two of said walls being parallel to each other and having a row of spaced ridges on the inner surfaces of said parallel walls;
b) vertical guide grooves in the inner surfaces of said parallel walls and a fitting hole in the lower portions of each of said parallel walls;
c) a long coiled spring for each of said rooms;
d) pushing blocks in each of said rooms in the base, each of said pushing blocks having a pulling grip extending downwardly from said rooms, a blocker extending upward from the pulling grip, said blocker engaging said long coiled spring, and an upper guide rail provided with a pushing piece thereon;
e) a position block attached to said base, said position block having two vertical ridges which fit into said two vertical guide grooves in said base, said position block further including a rod supporter having two parallel vertical walls and a rod pinched between said walls;
f) a fixing plate sustained on the rod of said position block having two spaced downward pinch arms forming an upper and a lower circular hole and having a flat square plate, said upper and lower circular holes being selectively fitted onto the rod in the position block;
g) a stop plate attached to said base having two projections on its lower sides which fit into the fitting holes in the parallel walls of said base, said stop plate being adapted to close a plurality of exits in one side of the base and to be pushed open by a cottonbud pushed by the pushing block out of one of the rooms in the base; and
h) a case body assembled on the base having its interior divided into a plurality of rooms with vertical separating boards equally spaced apart for storing cottonbuds, each of said vertical separating boards having a large opening in the middle portion facing towards the base, said rooms in said case body being in communication with the rooms in said base.

2. A cottonbud dispenser comprising:
a) a base including one or more vertical walls, a plurality of separate, lengthwise rooms, two walls parallel to the long access of said rooms, and a vertical guide groove located on an inner surface of one end of said parallel walls;
b) a case body attached to said base for storing elongated cottonbuds, the case body including a plurality of lengthwise rooms, each of which rooms is open to a respective one of the rooms in said base;
c) a pushing block slidably mounted in each room which may be impelled across a long axis of said room to eject a cottonbud from the dispenser;
d) a spring compressed by said pushing block when said block is impelled across said room, said spring returning said pushing block approximately to its original position when released;
e) an outlet in one of said rooms which is open to said room; and
f) a stop plate which covers said outlet but which is urged to an open position by a cottonbud when said pushing block ejects the cottonbud from the dispenser.

3. The dispenser of claim 2 including a position block having two ridges which fit into the two vertical guide grooves in said base, wherein said position block is positioned vertically with respect to said base when said ridges engage said guide grooves, and wherein said position block forms a wall of said base.

4. The dispenser of claim 3 wherein said position block further comprises a rod supporter having two outwardly extending spaced walls and a rod fixed between the walls, and a fixing plate having two spaced pinching arms open at one end forming holes adapted to fit on said rod.

5. The dispenser of claim 2 wherein the inner surfaces of each of the walls which are parallel to the long axis of said rooms contain a row of spaced ridges which engage spaces between ridges located on the lower portion of the corresponding walls of the case body.

* * * * *